United States Patent
King et al.

(10) Patent No.: US 9,907,736 B1
(45) Date of Patent: Mar. 6, 2018

(54) METAL OXIDE PARTICLE BOUND OXYBENZONE

(71) Applicant: INTERNATIONAL BUSINESS MACHINES CORPORATION, Armonk, NY (US)

(72) Inventors: Scott B. King, Rochester, MN (US); Brandon M. Kobilka, Tucson, AZ (US); Joseph Kuczynski, North Port, FL (US); Jason T. Wertz, Pleasant Valley, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 15/294,838

(22) Filed: Oct. 17, 2016

(51) Int. Cl.
| | | |
|---|---|---|
| *A61K 8/35* | (2006.01) | |
| *A61K 49/18* | (2006.01) | |
| *A61K 8/02* | (2006.01) | |
| *B82Y 5/00* | (2011.01) | |
| *A61K 8/29* | (2006.01) | |
| *A61K 8/22* | (2006.01) | |
| *A61K 8/26* | (2006.01) | |
| *A61K 8/27* | (2006.01) | |

(52) U.S. Cl.
CPC ............. *A61K 8/35* (2013.01); *A61K 8/0245* (2013.01); *A61K 8/22* (2013.01); *A61K 8/26* (2013.01); *A61K 8/27* (2013.01); *A61K 8/29* (2013.01); *B82Y 5/00* (2013.01); *A61K 2800/412* (2013.01); *A61K 2800/413* (2013.01)

(58) Field of Classification Search
CPC .................................. A61K 8/35; A61K 49/18
See application file for complete search history.

(56) References Cited

U.S. PATENT DOCUMENTS

| 8,895,042 B2 | 11/2014 | Mankovitz |
| 2006/0239941 A1 | 10/2006 | Park et al. |
| 2007/0071700 A1 | 3/2007 | Abhimanyu Pahl et al. |
| 2014/0170096 A1 | 6/2014 | Danovaro et al. |
| 2016/0008237 A1 | 1/2016 | Goldstein et al. |

OTHER PUBLICATIONS

Tibbetts, "Bleached,ButnotbytheSun:Sunscreen Linked to Coral Damage", EnvironHealthPerspect, Apr. 2008, 116(4): A173.*
Danovaro, R. et al., "Sunscreens Cause Coral Bleaching by Promoting Viral Infections" Environmental Health Perspectives (Apr. 2008) pp. 441-447, vol. 116, No. 4.

* cited by examiner

*Primary Examiner* — Carlos Azpuru
(74) *Attorney, Agent, or Firm* — Tutunjian & Bitetto, P.C.; Robert R. Williams (57) ABSTRACT

A method for forming a benzophenone derivative product that resistant to absorption by living tissue that includes binding a benzophenone-containing compound with an oxide-containing particle by acid-catalyzed condensation or Friedel-Crafts acetylation to provide a benzophenone derivative having a microscale size. The benzophenone derivative can then be mixed into a lotion. The microscale size of the benzophenone derivative obstructs absorption by cell tissue. The benzophenone derivative may be an oxybenzone derivative.

17 Claims, 6 Drawing Sheets

METAL OXIDE PARTICLE BOUND OXYBENZONE

BACKGROUND

Technical Field

The present disclosure generally relates to benzophenone including formulations, and more particularly to binding oxybenzones to a particle to prevent leaching into the environment.

Description of the Related Art

Sunscreens are products combining several ingredients that help prevent the sun's ultraviolet (UV) radiation from reaching the skin. Two types of ultraviolet radiation, i.e., UVA and UVB, damage the skin, age it prematurely, and increase the risk of skin cancer. It is believed that UVB is the principle form of radiation behind sunburn, while UVA rays, which penetrate the skin more deeply, are associated with wrinkling, leathering, sagging, and other light-induced effects of aging. The most common sunscreens on the market contain chemical filters that include a combination of two to six of the following active ingredients: oxybenzone, avobenzone, octisalate, octocrylene, homosalate and octinoxate. One problematic chemical that is used in sunscreen is oxybenzone, found in nearly every chemical sunscreen. In some instances, oxybenzone can penetrate the skin, cause allergic skin reactions, and may disrupt hormones. It has also been determined that there may be a link between higher concentrations of oxybenzone and its metabolites in the human body and increased risk of endometriosis and lower birthweight. Further, oxybenzone has been implicated as a major contributor to the bleaching of coral reefs worldwide. Consequently, a need exists to mitigate the harmful effects of oxybenzone while maintaining its beneficial UV filtering properties.

SUMMARY

In accordance with an embodiment of the present disclosure, a method for forming a benzophenone, such as oxybenzone, for use in products that absorb or filter ultra-violet light is described herein. The benzophenone derivative, e.g., oxybenzone derivative, is processed using the methods disclosed herein to prevent leaching from consumer products, such as sunscreen lotions and cosmetic products, into elements of the environment, such as into coral reefs.

In one embodiment, a method for forming the benzophenone derivative product is provided that is resistant to absorption by living tissue. The method may include binding a benzophenone-containing compound with an oxide-containing particle by acid-catalyzed condensation to provide a benzophenone derivative having a microscale size. The benzophenone derivative may then be mixed into a lotion. The microscale size of the benzophenone derivative obstructs absorption by cell tissue.

In another aspect, a method for forming a benzophenone derivative that is resistant to absorption by living matter is provided that includes binding a benzophenone with an oxide-containing particle by Friedel-Crafts acylation. In one embodiment, the method for forming the benzophenone derivative that is resistant to absorption by living tissue includes binding a benzophenone-containing composition with an oxide-containing particle by Friedel-Crafts acylation to provide the benzophenone derivative having a microscale size; and mixing the benzophenone derivative having the microscale size into a lotion product, wherein said microscale size obstructs absorption by cell tissue.

In another aspect, a lotion is provided including a benzophenone derivative that is bound to a metal oxide particle, wherein the compound size of the benzophenone derivative that is bound to the metal oxide particle is on a microscale.

These and other features and advantages will become apparent from the following detailed description of illustrative embodiments thereof, which is to be read in connection with the accompanying drawings.

BRIEF DESCRIPTION OF THE DRAWINGS

The following description will provide details of preferred embodiments with reference to the following figures wherein.

DETAILED DESCRIPTION

Detailed embodiments of the claimed structures and methods are disclosed herein; however, it is to be understood that the disclosed embodiments are merely illustrative of the claimed structures and methods that may be embodied in various forms. In addition, each of the examples given in connection with the various embodiments are intended to be illustrative, and not restrictive. Further, the figures are not necessarily to scale, some features may be exaggerated to show details of particular components. Therefore, specific structural and functional details disclosed herein are not to be interpreted as limiting, but merely as a representative basis for teaching one skilled in the art to variously employ the methods and structures of the present disclosure.

References in the specification to "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The present disclosure generally relates to benzophenone-containing formulations, and more particularly to binding oxybenzones to a particle to prevent leaching into the environment. Oxybenzone is typically used in sunscreen, as well as cosmetic applications. Most common sunscreens on the market contain chemical filters, which can include a combination of two to six of the following active ingredients: oxybenzone, avobenzone, octisalate, octocrylene, homosalate, and octinoxate. Mineral sunscreens use zinc oxide and/or titanium dioxide. Benzophenone, e.g., Benzophenone-3, which is also referred to as oxybenzone, has been associated with mimicking hormones or causing skin allergies in humans, which raises questions about unintended effects on human health from frequent sunscreen application. Furthermore, it has been determined that leaching of benzophenones, such as oxybenzone, may negatively cause bleaching of the coral reefs. It has been determined that mineral sunscreens, such as those based on zinc oxide or titanium dioxide, are of a lower toxicity than their chemical filter counterparts, such as those including benzophenones, e.g., oxybenzone. Although originally white in color, the white tint of mineral-based sunscreens can be reduced by reducing the particle size of the metal oxide particle therein into the nanoscale realm, i.e., less than 1 micron in size. Although reducing the particle size can reduce the incidence of the white coloring in cosmetic product, nanoscale particles are a regulatory problem due to variations in their size and shape, as well as surface area and coatings that may be present thereon. Additionally, consumer preference indicates an advantage in sunscreens containing chemical filters.

Figure 1:
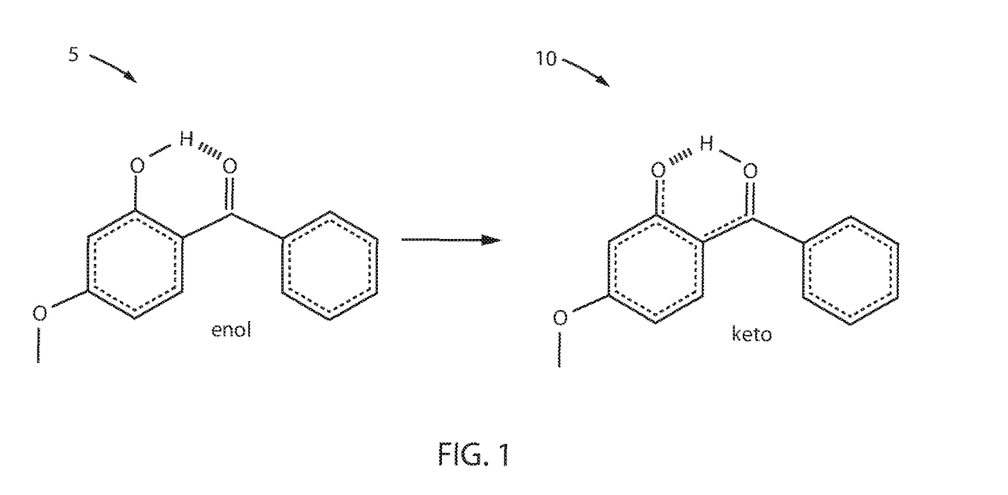
FIG. 1 is a chemical structure diagram illustrating one embodiment of excited state enol to keto tautomerization that is consistent with absorbing UVA/B sunlight, in accordance with an embodiment of the present disclosure.

Chemical filters function by absorbing UVA/B sunlight and converting it to vibrational energy. In some embodiments, in which the chemical filter is provided by oxybenzone, the photoprotective properties can be understood in terms of an initial ultrafast excited state enol (identified by reference number 5) to keto (identified by reference number 10) tautomerization, as depicted in FIG. 1. This is followed by efficient internal conversion, and subsequent vibrational relaxation to the ground state (enol) tautomer.

Figure 2:
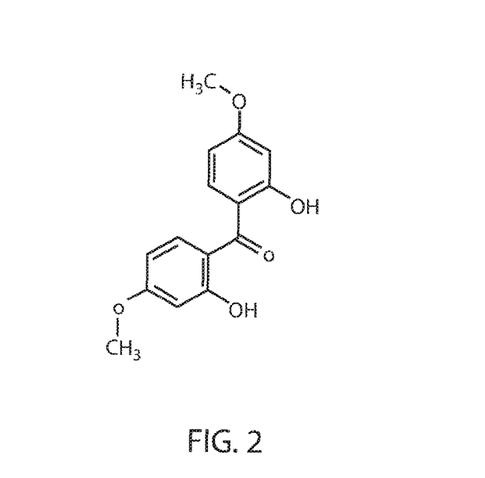
FIG. 2 is chemical structure diagram depicting one embodiment of oxybenzone, in accordance with one embodiment of the present disclosure.

In order to reduce or substantially eliminate the aforementioned health and environmental pollution risks, the disclosed methods and compositions provide for derivitizing oxybenzone (as depicted in FIG. 2) or an analogous compound, such as other benzophenones, and binding it with an oxide-containing particle, such as a metal oxide, e.g., zinc oxide (ZnO) or titanium dioxide ($TiO_2$). By increasing the size of the compound by binding it with the oxide-containing particle, the compound can be obstructed from dermal absorption by living tissue, e.g., cells.

The oxybenzone structure depicted in FIG. 2 is a hydroxyl-functionalized derivative of the enol form depicted in FIG. 1. In this embodiment, a hydroxyl group (—OH) provides a functional handle by which the compound may be bound to an oxide-containing particle, such as a metal oxide, e.g., titanium dioxide ($TiO_2$) or zinc oxide (ZnO). Although the methods and structures for increasing the oxybenzone-containing compound size to avoid absorbing into cell structures, such as human tissue or coral reefs, are described herein specifically to oxybenzone, the present disclosure is not limited to only this benzophenone. For example, in addition to Benzophenone-3, i.e., oxybenzone, being employed in sunscreens as one application for the compounds formed herein, sunscreens may also include Benzophenone-4 to protect the skin from UV rays. More generally, Benzophenone-1, Benzophenone-3, Benzophenone-4, Benzophenone-5, Benzophenone-9, and Benzophenone-11 may be used in cosmetics and personal care products to protect the products or the substrate to which the product is applied from deterioration by absorbing, reflecting, or scattering UV rays. The methods of binding oxide-containing particles that are described herein to oxybenzone can be equally applicable to the aforementioned benzophenones. In some embodiments of the methods described herein, oxybenzone, i.e., benzophenone-3 (oxybenzone), may be substituted with benzophenones selected from the group consisting of Benzophenone-1 (2,4-dihydroxybenzophenone), Benzophenone-2 (2,2',4,4'-tetrahydroxybenzophenone), Benzophenone-4 (sulisobenzone), Benzophenone-5 (sulisobenzone sodium), Benzophenone-6 (2,2'-dihydroxy-4,4'-dimethoxybenzophenone), Benzophenone-7 (5-chloro-2-hydroxybenzophenone), Benzophenone-8 (dioxybenzone), Benzophenone-9 (sodium 2,2'-dihydroxy-4,4'-dimethoxybenzophenone-5,5'-disulfonate), Benzophenone-10 (mexenone, 2-hydroxy-4-methoxy-4'-methylbenzophenone), Benzophenone-11 (benzophenone-2 and benzophenone-6), Benzophenone-12 (octabenzone), and combinations thereof. It is further noted that the methods and structures may also employ compounds, such as avobenzone, octisalate, octocrylene, homosalate, and octinoxate, as substitutes for oxybenzone.

It is also noted that although the following descriptions provides titanium dioxide ($TiO_2$) and zinc oxide (ZnO) as examples of oxide-containing particles that are bound to the benzophenone compound, e.g., oxybenzone compound, the present disclosure is not limited to only these metal oxides. In some examples, the oxide-containing particle is a metal oxide selected from the group consisting of titanium dioxide ($TiO_2$), tantalum oxide ($TaO_2$), aluminum oxide ($A_{12}O_3$), zinc oxide ($ZnO_2$), and combinations thereof. In some examples, titanium dioxide is employed, because of the non-toxic nature of the material.

In some embodiments, the titanium dioxide employed for the oxide-containing particles may be in the form of nanoparticles, i.e., particles having a nanoscale. In some examples, the oxide-containing particles having the nanoscale have a diameter that ranges from 5 nm to 100 nm. In other examples, the oxide-containing particles having a nanoscale dimension may have a diameter ranging from 10 nm to 50 nm. In further examples, the oxide-containing particles having the nanoscale dimension ranging from 15 nm to 25 nm. It is noted that the diameter of the nanoscale particles of titanium dioxide may also be equal to 5 nm, 10 nm, 15 nm, 20 nm, 25 nm, 30 nm, 35 nm, 40 nm, 45 nm, 50 nm, 55 nm, 60 nm, 65 nm, 70 nm, 75 nm, 80 nm, 85 nm, 90 nm and 95 nm, as well as any range of dimensions including a lower limit and upper limit selected from the above examples.

In some embodiments, the nanoparticles of titanium dioxide that may be prepared for binding to benzophenones, such as oxybenzone, may include nano titanium dioxide having a particle size on the order of 20 nm and having a purity greater than 98%. In some examples, the purity of the titanium dioxide may be 99.5% pure.

Figure 3:
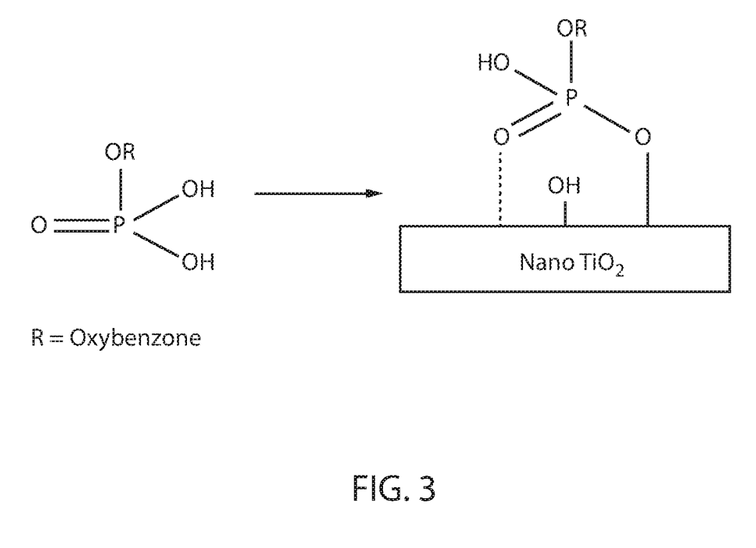
FIG. 3 is a schematic illustrating the interaction between an oxide-containing particle binding to a phosphate during a surface modification step of the binding process.
Figure 7:
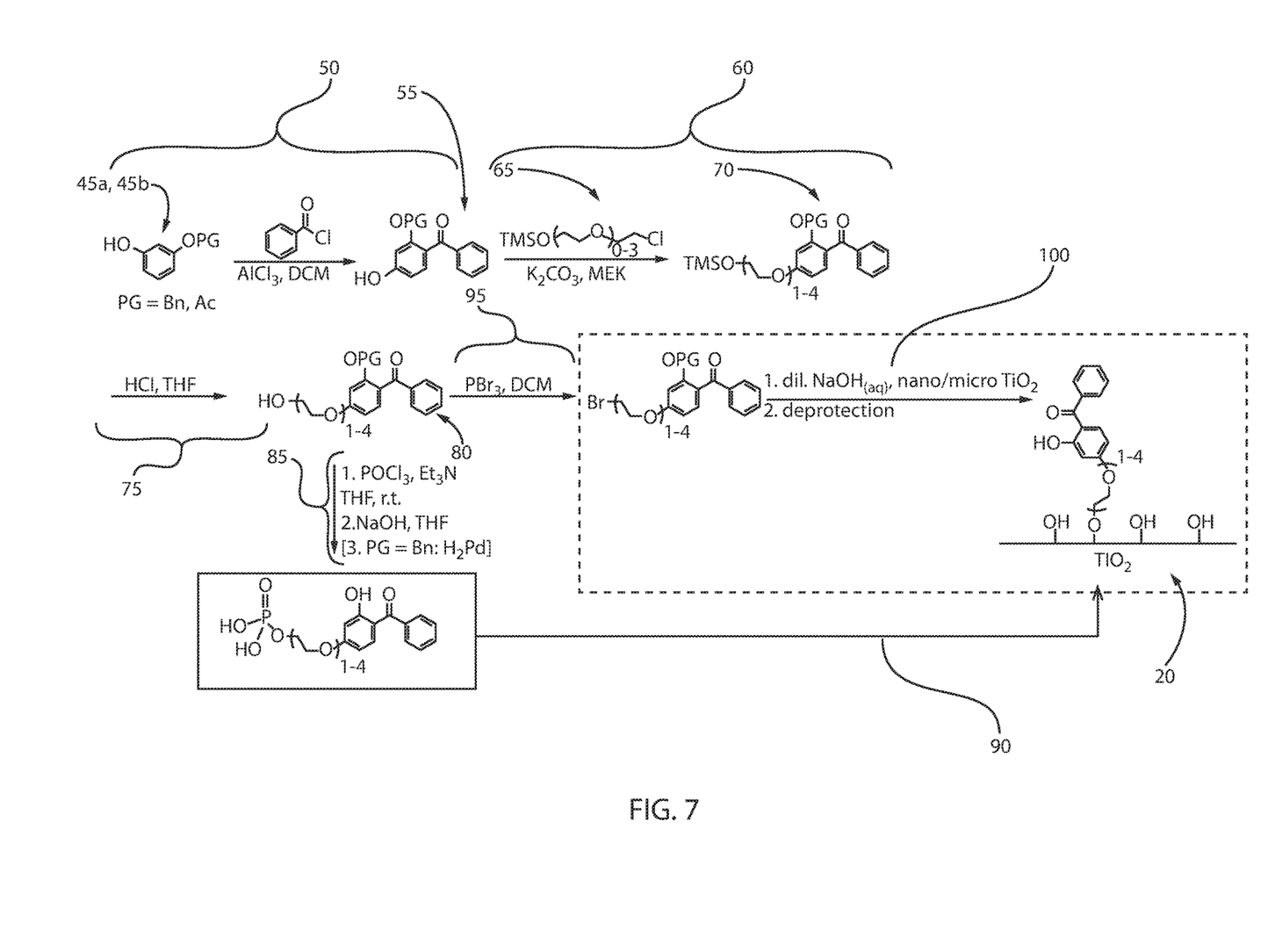
FIG. 7 is a chemical structure diagram illustrating one embodiment of forming a protected hydroxyl-oxybenzone derivative synthesized via a Friedel-Crafts acylation.

In some embodiments, a hydroxyl group (—OH) of the benzophenone-containing composition provides a functional handle by which the compound may be bound to an oxide-containing particle, such as a metal oxide, e.g., titanium dioxide ($TiO_2$) or zinc oxide (ZnO). Employing a hydroxyl group as the function handle to bind an oxide-containing particle, e.g., titanium dioxide, to the oxybenzone compound is similar to the mechanism by which titanium dioxide is bound to phosphates, as depicted in FIG. 3. In FIG. 3, the titanium dioxide was surface modified with 2-aminoethyl dihydrogen phosphate (AP), in which the surface modification is depicted in FIG. 3. In FIG. 3, the R group is an ether-linked oxybenzone analogue as depicted in FIG. 7.

Figure 4:
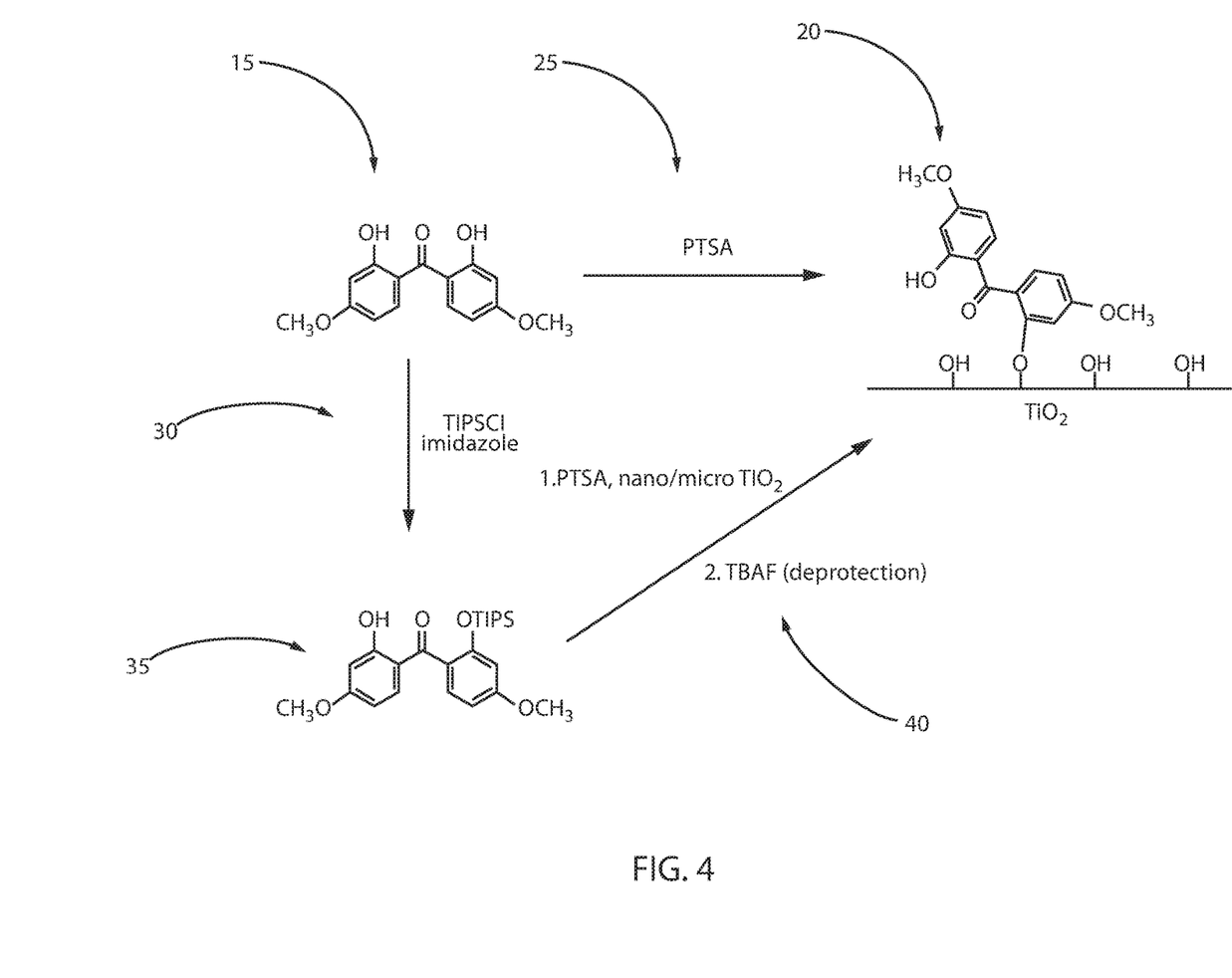
FIG. 4 is a chemical structure diagram illustrating one embodiment for binding oxybenzone to titanium dioxide nanoparticles that employs an acid-catalyzed condensation, in accordance with one embodiment of the present disclosure.

FIG. 4 is a chemical structure diagram illustrating one embodiment for binding oxybenzone to titanium dioxide nanoparticles that employs an acid-catalyzed condensation, e.g., by employing a sulfonic acid. A condensation reaction is a chemical reaction in which two molecules or moieties, often functional groups, combine to form a larger molecule, together with the loss of a small molecule, e.g., water, hydrogen chloride, methanol, or acetic acid. In one embodiment, binding oxybenzone to titanium dioxide particles is accomplished by taking the symmetric 2,2'-hydrozy-4,4'-methoxybenzophenone molecule (identified by reference number 15), and directly binding it to the titanium dioxide particle via an acid-catalyzed condensation with p-toluensulfonic acid (PTSA) (identified by reference number 25). p-Toluenesulfonic acid (PTSA or pTsOH) or tosylic acid (TsOH) is an organic compound with the formula $CH_3C_6H_4SO_3H$. As with other sulfonic acids, TsOH is a strong organic acid, e.g., having an acidity on the order of −2.8 (water). Also, unlike some strong mineral acids (especially nitric acid, sulfuric acid, and perchloric acid), TsOH is non-oxidizing. Although the sulfonic acid described above for the reaction depicted in FIG. 4 is p-Toluenesulfonic acid (PTSA or pTsOH), the present disclosure is not limited to only this example. It has been contemplated that p-toluenesulfonic acid (PTSA or pTsOH) may be substituted with one of benzenesulfonic acid or sulfanilic acid.

Binding the oxide-containing particle, e.g., titanium dioxide nanoparticle, by acid-catalyzed condensation using p-Toluenesulfonic acid (PTSA or pTsOH) provides an benzophenone-containing compound (identified by reference number 20) having a size suitable to avoid being absorbed into cell structures, such as human tissue or coral reefs. The benzophenone that is bound to the oxide-containing particle using the method described above can provide a benzophenone-containing compound (identified by reference number 20) having a size ranging from 10 μm to 100 μm. In other examples, the size of the benzophenone-containing compound, e.g., oxybenzone, that is bound to an oxide-containing particle, such as titanium dioxide, has a size that may be equal to 10 μm, 15 μm, 20 μm, 25 μm, 30 μm, 35 μm, 40 μm, 45 μm, 50 μm, 55 μm, 60 μm, 65 μm, 70 μm, 75 μm, 80 μm, 85 μm, 90 μm, 95 μm and 100 μm, as well as any range of dimensions having a lower value and an upper value each provided by one of the aforementioned example dimensions.

Still referring to FIG. 4, in another embodiment, it is possible to protect one of the hydroxyl groups (—OH) of the symmetric 2,2'-hydrozy-4,4'-methoxybenzophenone molecule (identified by reference number 15) using a silyl chloride (identified by reference number 30), such as triisopropylsilyl chloride (TIPSCI)($[(CH_3)_2CH]_3SiCl$). TIPSCI may be chosen because of its non-polar nature, which can facilitate purification of a triisopropylsilyl ether (TIPS) protected product. In some embodiments, protecting the hydroxyl group may further include treating the symmetric 2,2'-hydrozy-4,4'-methoxybenzophenone molecule (identified by reference number 15) using a silyl chloride (identified by reference number 30), such as triisopropylsilyl chloride (TIPSCI)($[(CH_3)_2CH]_3SiCl$), in combination with a solvent such, as imidazole. Imidazole is an organic compound with the formula $C_3N_2H_4$.

Still referring to FIG. 4, the mono-protected derivative (identified by reference number 35) that was produced by reaction with the silyl chloride, or similar composition, with the benzophenone compound, e.g., the 2,2'-hydrozy-4,4'-methoxybenzophenone molecule (identified by reference number 15), is then reacted with the titanium dioxide ($TiO_2$) nanoparticles to provide the benzophenone compound (identified by reference number 20) having dimensions sufficient to obstruct absorption into cell structures, e.g., human tissue or coral reefs. In some examples, the binding of the mono-protected derivative of the oxybenzone to the titanium dioxide particles may be accomplished by an acid-catalyzed condensation with p-Toluensulfonic acid (PTSA) (identified by reference number 40). The present disclosure is not limited to only this example, as p-toluenesulfonic acid (PTSA or pTsOH) can be substituted with one of benzenesulfonic acid or sulfanilic acid in some other embodiments of the present disclosure. In some embodiments, the binding of the mono-protected derivative of the oxybenzone to the titanium dioxide particles may further include a deprotection step. In some embodiments, the deprotection step is needed to reform the hydroxyl group that can be necessary for the keto-enol tautomerism of FIG. 1. The unprotected OH of the mono-protected derivative (identified by reference number 35) condenses with the nano $TiO_2$ to form the surface bound molecule in 20. Deprotection of the second OH group re-enables the keto-enol reaction.

For example, deprotection of the mono-protected derivative of the oxybenzone for the purposes of binding to oxide-containing particles, such as titanium dioxide particles, may include a treatment with an ammonium salt, such as tetra-n-butylammonium fluoride, which is commonly abbreviated as TBAF and n-$Bu_4NF$. TBAF is a quaternary ammonium salt with the chemical formula $(CH_3CH_2CH_2CH_2)_4N^+F^-$.

The benzophenone that is bound to the oxide-containing particle using the method described above, including the step of providing a mono-protected derivative (identified by reference number 35) by reaction with a silyl chloride, can provide a benzophenone-containing compound (identified by reference number 20) having a size ranging from 10 μm to 100 μm. In other examples, the size of the benzophenone-containing compound, e.g., oxybenzone, that is bound to an oxide-containing particle, such as titanium dioxide, has a size that may be equal to 10 μm, 15 μm, 20 μm, 25 μm, 30 μm, 35 μm, 40 μm, 45 μm, 50 μm, 55 μm, 60 μm, 65 μm, 70 μm, 75 μm, 80 μm, 85 μm, 90 μm, 95 μm, and 100 μm, as well as any range of dimensions having a lower value and an upper value each provided by one of the aforementioned example dimensions.

Binding the oxide-containing particle, e.g., titanium dioxide nanoparticle, by acid-catalyzed condensation using p-toluenesulfonic acid (PTSA or pTsOH) provides an oxybenzone-containing compound (identified by reference number 20) having a size suitable to avoid absorbing into cell structures, such as human tissue or coral reefs.

Other embodiments of the present disclosure may include synthesizing "tetherable" oxybenzone derivatives in order to provide compounds that are suitable for absorbing UV light while avoiding absorption into living tissue, e.g., cells. Typically, in accordance with these embodiments, oxybenzone, or a like oxybenzone compound, is synthesized via Friedel-Crafts acylation of 3-methoxyphenol by benzoyl chloride. Friedel-Crafts acylation includes an electrophilic aromatic substitution that allows for the synthesis of monoacylated products from reactions between arenes and acyl chlorides or anhydrides. The products are deactivated, and typically do not undergo a second substitution. In some instances, a stoichiometric amount of the Lewis acid catalyst is required, because both the substrate and the product form complexes. The methods and structures provided herein that provide benzophenone-containing compounds, e.g., oxybenzone, that can be bound to an oxide-containing particle, such as titanium dioxide particles, by synthesizing "tetherable" derivatives via Friedel-Crafts acylation are now described in greater detail with reference to FIGS. 5-8.

Figure 5:
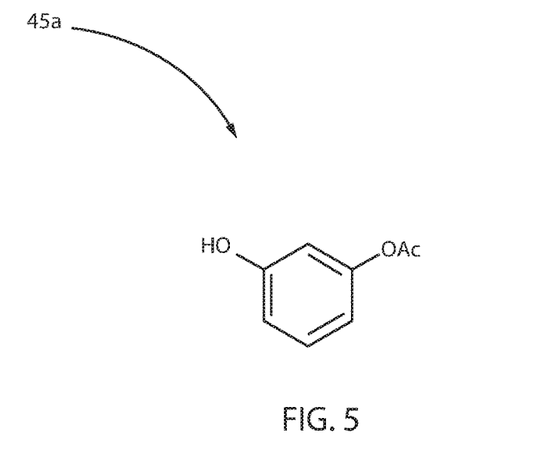
FIG. 5 is a chemical structure diagram illustrating one embodiment of monoacetate, as used in accordance with the present disclosure.

In some embodiments, the methods may employ a mono-protected resorcinol, as depicted in FIG. 5. Resorcinol (or resorcin) having the chemical formula $C_6H_6O_2$ is a benzenediol (m-dihydroxybenzene). Resorcinol may be selected because it allows one of the hydroxyl groups to be reacted chemically, while leaving the other one, i.e., a second hydroxyl group, available to be functionalized further. In one example, the starting material for forming oxybenzone derivatives and their binding to oxide-containing particles, such as nanoscale titanium dioxide particles, may begin with resorcinol monoacetate ($C_8H_8O_3$), as depicted in FIG. 5.

Figure 6:
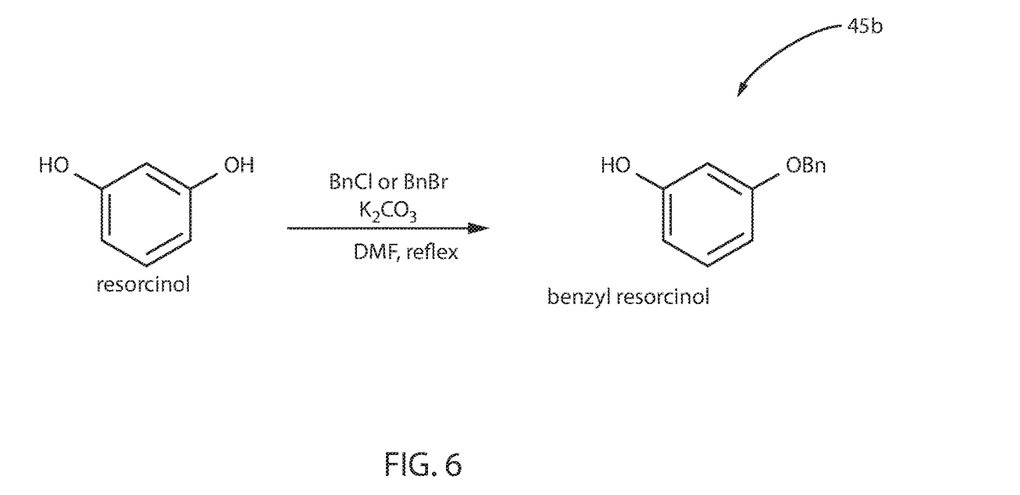
FIG. 6 is a chemical structure diagram illustrating one embodiment of 3-benzylphenol ether ($C_{13}H_{12}O$) or another like ether derivative.

Referring to FIG. 6, in other embodiments, the starting material may be 3-benzylphenol ether ($C_{13}H_{12}O$) or another like ether derivative. 3-benzylphenol ether ($C_{13}H_{12}O$) may be synthesized by reacting at least one of benzyl bromide (BnBr), benzyl chloride (BnCl), and potassium carbonate ($K_2CO_3$) with resorcinol. In another example, 3-benzylphenol ether ($C_{13}H_{12}O$) may be synthesized by reacting dimethylformamide (DMF) $(CH_3)_2NC(O)H$ with resorcinol under reflux conditions. Reflux is a technique involving the condensation of vapors and the return of this condensate to the system from which it originated.

Referring to FIG. 7, beginning from resorcinol monoacetate, as depicted in FIG. 5, or 3-benzylphenol ether, synthesized in accordance with the reactions illustrated in FIG. 6, a protected hydroxy-oxybenzone derivative (identified by reference number 55) is synthesized via a Friedel-Crafts acylation, in which the Friedel-Crafts acetylation is depicted as the first reaction identified by reference number 50. During the Friedel-Crafts acetylation reaction, aluminum chloride ($AlCl_3$) may be employed as a catalyst in a solution of dichloromethane (DCM). It is noted that other Lewis acids may be employed in addition to aluminum chloride ($AlCl_3$). For example, ferric chloride ($FeCl_3$) and boron trichloride ($BCl_3$) have been contemplated as alternatives to aluminum chloride at this stage of the process flow.

Referring to FIG. 7, in a following reaction identified by reference number 60, the unprotected hydroxyl group of the protected hydroxy-oxybenzone derivative that was synthesized by the Friedel-Crafts acylation is reacted with a silyl-protected version of a chloroethylene ether chain (illustrated by reference number 65) via nucleophilic substitution. The term "nucleophilic substitution" denotes a class of reactions in which an electron rich nucleophile selectively bonds with or attacks the positive or partially positive charge of an atom or a group of atoms to replace a leaving group. The above referenced silyl-protected version of the choloroethylene ether chain may be synthesized in accordance with the reactions illustrated in FIG. 8.

Figure 8:
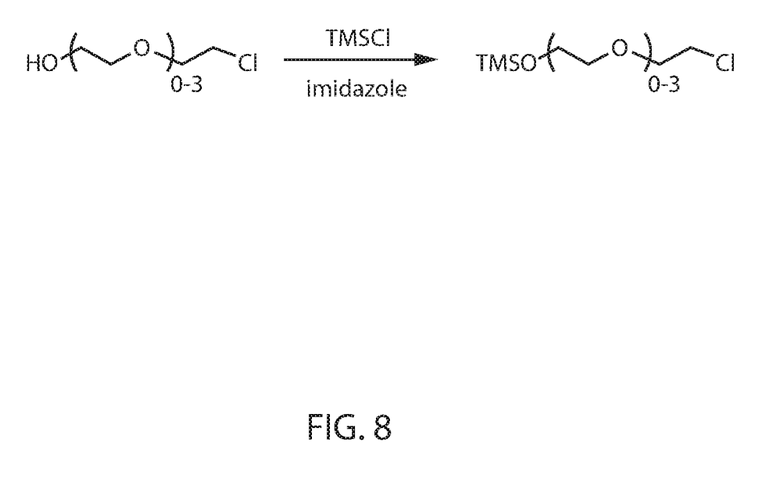
FIG. 8 illustrates one embodiment of using a reaction with a silyl chloride to protect one of the hydroxyl groups (—OH) of a chloroethylene ether chain.

FIG. 8 illustrates one embodiment of using a reaction with a silyl chloride to protect one of the hydroxyl groups (—OH) of a chloroethylene ether chain. The silyl chloride may be trimethylsilyl chloride, also known as chlorotrimethylsilane, which is an organosilicon compound (silyl halide) having the formula $(CH_3)_3SiCl$, and often abbreviated $Me_3SiCl$ or TMSCl. The reaction of the TMSCl and the chloroethylene ether chain may be carried out in a solvent such as imidazole. Other common trialkylsilyl (chloride) groups may also be used at this stage of the present disclosure, such as tert-butyldimethyl (TBDMS), triethylsilyl (TES), tert-butyldiphenylsilyl (TPS), and triisopropylsilyl (TIPS).

As noted above, the unprotected hydroxyl group (—OH) of the protected hydroxy-oxybenzone derivative that was synthesized by the Friedel-Crafts acylation is reacted with a silyl-protected version of a chloroethylene ether chain via nucleophilic substitution, in which the nucleophilic substitution is depicted by reference number 60. The nucleophilic substitution reaction may further include the application of a potassium carbonate ($K_2CO_3$) solution in a methyl ethyl ketone ($CH_3C(O)CH_2CH_3$)(MEK) solvent.

The TMS-protected ethyl ether linked protected-oxybenzone identified by reference number 70 may be 2-benzoyl-5-(2-((trimethylsilyl)oxy)ethoxy)phenyl acetate when N=1 and PG=acetate. In another embodiments, the TMS-protected ethyl ether linked protected-oxybenzone identified by reference number 70 may be 2-benzoyl-5-(2-((trimethylsilyl)oxy)ethoxy)ethoxy)phenyl acetate when N=2 and PG=acetate. In yet another embodiment, the TMS-protected ethyl ether linked protected-oxybenzone identified by reference number 70 may be 2-benzoyl-5-(2-((trimethylsilyl)oxy)ethoxy)ethoxy)ethoxy)phenyl acetate, when N=3 and PG=acetate. In an even further embodiment, the TMS-protected ethyl ether linked protected-oxybenzone identified by reference number 70 may be (2-(benzyloxy)-4-(2-((trimethylsilyl)oxy)ethoxy)phenyl)(phenyl)methanone, when N=1 and PG=benzyl. It is noted that the above compositions for the TMS-protected ethyl ether linked protected-oxybenzone identified by reference number 70 are only illustrative and other compositions may also be suitable for use herein.

Still referring to FIG. 7, the silyl protecting group can then be removed under acidic conditions. The reaction for removing the silyl protecting group is identified by reference number 75. For example, the silyl protecting group may be removed using hydrochloric acid (HCl) in a solvent of tetrahydrofuran (THF). THF is an organic solvent with the formula $(CH_2)_4O$. One embodiment of the benzophenone-containing compound following removal of the silyl protecting group is identified by reference number 80, which is a deprotected ethyl ether linked protected-oxybenzone.

In one embodiment, the deprotected ethyl ether lined protected oxybenzone may be 2-benzoyl-5-(2-hydroxyethoxy)phenyl acetate when n=1 and PG=acetate. In another embodiment, the deprotected ethyl ether lined protected oxybenzone may be (2-(benzyloxy)-4-(2-hydroxyethoxy)phenyl)(phenyl)methanone when n=1 and PG=Benzyl group (Bn).

Removing the silyl protecting group exposes a terminal hydroxyl group (—OH) of the benzophenone-containing compound. The resulting terminal hydroxyl group is converted into a phosphoric acid via a reaction with phosphorous oxychloride ($POCl_3$) that is identified by reference number 85 in FIG. 7. It is noted that phosphorus oxychloride ($POCl_3$) is only one example of a composition that is suitable for reaction with the benzophenone-containing compound to convert the terminal hydroxyl group to a phosphoric acid. Other examples of compositions suitable for providing this purpose may be selected from the group consisting of thiophosphoryl chloride, phosphorus trichloride, phosphorus pentachloride and combinations thereof. The reaction to convert the terminal hydroxyl group to phosphoric acid, e.g., with $POCl_3$, may further include a Lewis base catalyst, such as Triethylamine ($Et_3N$) having the formula $N(CH_2CH_3)_3$, and a solvent, such as tetrahydrofuran (THF). After a subsequent deprotection, the hydroxyl-terminated chain-functionalized oxybenzone is bound to an oxide containing particle, e.g., titanium nanoparticle. The hydroxyl-terminated chain-functionalized oxybenzone may be dissolved or suspended in distilled water. Nano or micro titanium dioxide ($TiO_2$) may be added into the oxybenzone molecule solution and may be stirred for 24 hours at room temperature, e.g., 20° C. to 25° C. The reaction mixture may contain a co-solvent such as ethanol, isopropanol, tetrahydrofuran, or ethanol to help dissolve the oxybenzone molecule. The reaction mixture may also be biphasic, wherein the organic layer is a solvent suitable for dissolving the oxybenzone molecule, such as dichloromethane, diethyl ether, toluene, etc., and the TiO2 particles are suspended primarily in the aqueous phase. Such as biphasic reaction mixture may contain a phase transfer agent, such as aliquot 336 or tetra-n-butyl ammonium bromide. Then the mixture may be centrifuged for 30 min. The resulted powders may be eluted with distilled water and, afterward, may be dried in an oven at 100° C. for 12 h. The deprotection may be provided by reaction with sodium hydroxide (NaOH) in a solvent, such as tetrahydrofuran (THF). The deprotection and binding reactions are identified by reference number 90.

The interaction of the benzophenone-containing compound, e.g., oxybenzone, having a terminal hydroxyl group that is converted to a phosphoric acid with the surface of a oxide-containing particle, such as a titanium dioxide nanoparticle, is described above with reference to FIG. 3.

The benzophenone that is bound to the oxide-containing particle using the method described above with reference to FIG. 7 can provide a benzophenone-containing compound (identified by reference number 20) having a size ranging from 10 μm to 100 μm. In other examples, the size of the benzophenone-containing compound, e.g., oxybenzone, that is bound to an oxide-containing particle, such as titanium dioxide, has a size that may be equal to 10 μm, 15 μm, 20 μm, 25 μm, 30 μm, 35 μm, 40 μm, 45 μm, 50 μm, 55 μm, 60 μm, 65 μm, 70 μm, 75 μm, 80 μm, 85 μm, 90 μm, 95 μm and 100 μm, as well as any range of dimensions having a lower value and an upper value each provided by one of the aforementioned example dimensions. The benzophenone-containing compound, e.g., oxybenzone, having the above referenced sizes is suitable for avoiding absorbing of benzophenone-containing compounds into cell structures, such as human tissue or coral reefs.

In another embodiment, to bind benzophenone-containing compounds, e.g., oxybenzone, to oxide-containing particles, e.g., titanium dioxide, the hydroxyl group of the benzophenone-containing compound following removal of the silyl protecting group, as is identified by reference number 80 in FIG. 7, is converted to a bromide and then bound to the titanium nanoparticle via nucleophilic substitution chemistry. The reaction for conversion of the terminal hydroxyl group of the benzophenone-containing compound to a bromide is illustrated by reference number 95. The conversion to a bromide may include reaction with phosphorus tribromide ($PBr_3$) in a solution of dichloromethane (DCM). It is noted that phosphorus tribromide ($PBr_3$) is only one example of a composition for converting the terminal hydroxyl group of the benzophenone-containing compound to a bromide. In other examples, the composition for converting the hydroxyl group to a bromide may include phosphorus pentabromide or phosphorus oxybromide.

The bromide functionalized benzophenone-containing compound, e.g., oxybenzone, is then bound to an oxide-containing particle, e.g., titanium nanoparticle. The bromo-terminated chain-functionalized oxybenzone may be dissolved in an organic solvent suitable nucleophilic substitution chemistry, such as diethyl ether, tetrahydrofuran, dioxane, dichloromethane, DMF, DMSO, etc. Nano or micro sized titanium dioxide ($TiO_2$) may be added into the oxybenzone molecule solution and may be stirred for 24 hours at room temperature or at reflux. The solvent may then be remove in vacuo or by aqueous workup and extraction. Then the mixture may be centrifuged for 30 minutes followed by a rinse with water or organic solvents, and may be centrifuged again. The centrifugation and rinsing process may be repeated multiple times. The resulted powders may be eluted with distilled water and, afterward, may be dried in an oven at 100° C. for 12 h. The deprotection, i.e., removal of the acetate or benzyl group, i.e., the protecting group on the oxybenzone hydroxyl group, may occur after the binding reaction, but this could also be accomplished prior to binding, if necessary. Deprotection may be provided by reaction with sodium hydroxide (NaOH) in a solvent, such as tetrahydrofuran (THF).

Other particles can be used in the place of the titanium dioxide nanoparticles, e.g., glass microbeads, with a particle size large enough to prevent deep penetration into the dermal layer and absorption into the body. In another embodiment, the particle can be functionalized further at remaining free hydroxyl groups with other compounds as desired for sunscreen formulations by those skilled in the art.

Any of the oxide particle bound benzophenone-containing compounds, e.g., oxybenzone-bound titanium nanoparticles, are then incorporated into sunscreen formulations. The sunscreen formulations suitable for use with the methods and compositions disclosed herein may include many combinations of synthetic and natural ingredients. A formulation is generally geared towards a specific SPF rating or the needs of a specific consumer group. Some embodiments employed herein include oxybenzone-containing compounds that are bound to nanoparticles of titanium dioxide for the active ingredient of the sunscreen. In addition to the sunscreening active ingredients, the formulations contemplated herein are typically emulsions such as lotions and creams, and therefore will contain several other components selected by the formulator from water, emulsifiers, emollients, fragrances, preservatives, vitamins, humectants, skin conditioners, antioxidants, waterproofing agents, and others. Antioxidants are often combined with titanium dioxide to slow down the oxidation of oils and thereby delay the deterioration of the lotion. Some examples of natural antioxidants are vitamins E and C, rice bran oil, and sesame seed oil. Another popular antioxidant in the natural category is green tea. Some sunscreen products also contain skin soothing and moisturizing additives such as aloe and chamomile.

Formulating the sunscreen lotion may begin with purifying water. Reverse osmosis extracts pure, fresh water by forcing water under pressure through a semipermeable membrane which separates pure water molecules from salts and other impurities. The active ingredients of the sunscreen lotion may then be mixed with the purified water. In some embodiments, the sunscreen lotion may be an emulsion that is formed by a process sequence that includes adding flake/powder ingredients to the oil being used to prepare the oil phase. The active ingredients may then be dispersed in the oil phase. The oxide particle bound benzophenone-containing compounds are active ingredients. A water phase containing emulsifiers and stabilizers may then be prepared. The oil (including the premixed active ingredients) and water may then be mixed to form an emulsion. Forming the emulsion can be aided by heating to between 110° F.-185° F. (45° C.-85° C.) depending on the formulation and viscosity desired. Mixing may be continued until the desired properties of the end product is provided.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C). This may be extended, as readily apparent by one of ordinary skill in this and related arts, for as many items listed.

Having described preferred embodiments of a composition and method (which are intended to be illustrative and not limiting), it is noted that modifications and variations can be made by persons skilled in the art in light of the above teachings. It is therefore to be understood that changes may be made in the particular embodiments disclosed which are within the scope of the invention as outlined by the appended claims. Having thus described aspects of the invention, with the details and particularity required by the patent laws, what is claimed and desired protected by Letters Patent is set forth in the appended claims.

What is claimed is:

1. A method for forming a benzophenone derivative product that is resistant to absorption by living tissue comprising:
    binding a benzophenone-containing compound with an oxide-containing particle by acid-catalyzed condensation to provide the benzophenone derivative having a microscale size; and
    mixing the benzophenone derivative into a lotion, wherein said microscale size obstructs absorption by cell tissue.

2. The method of claim 1, wherein a hydroxyl group (—OH) of the benzophenone provides a functional handle for said binding to the oxide-containing particle.

3. The method of claim 1, wherein the oxide-containing particle has a nanoscale, wherein a diameter of said oxide-containing particle having said nanoscale ranges from 5 nm to 100 nm.

4. The method of claim 3, wherein the oxide-containing particle is a metal oxide selected from the group consisting of titanium dioxide ($TiO_2$), tantalum oxide ($TaO_2$), aluminum oxide ($Al_2O_3$), zinc oxide (ZnO), and combinations thereof.

5. The method of claim 1, wherein the acid-catalyzed condensation comprises reacting said benzophenone with a sulfonic acid to directly bind the benzophenone to the metal oxide particle.

6. The method of claim 5, wherein said benzophenone comprises a symmetric 2,2'-hydrozy-4,4'-methoxybenzophenone molecule, and said sulfonic acid comprises p-toluensulfonic acid (PTSA).

7. The method claim 6, wherein the binding of the benzophenone with the metal oxide particle comprises protecting one hydroxy group of the benzophenone by reaction with a silyl chloride prior to said acid-catalyzed condensation to directly bond the benzophenone to the metal oxide particle.

8. The method of claim 7, wherein the silyl chloride is tiisiopropylsilyl chloride (TIPSCI)($[(CH_3)_2CH]_3SiCl$).

9. The method of claim 1, wherein the benzophenone derivative with the oxide-containing particle having said microscale has a size ranging from 10 microns to 100 microns.

10. A method for forming a benzophenone derivative product that is resistant to absorption by living tissue comprising:
    binding a benzophenone including composition with an oxide-containing particle by Friedel-Crafts acylation to provide the benzophenone derivative having a microscale size; and
    mixing the benzophenone derivative having the microscale size into a lotion, wherein said microscale size obstructs absorption by cell tissue.

11. The method of claim 10, wherein the binding of the benzophenone including composition prior to binding to the oxide-containing particle comprises resorcinol, a benzylphenol ether or a combination thereof.

12. The method of claim 11, wherein the Friedel-Crafts acetylation reaction comprises aluminum chloride ($AlCl_3$) employed as a catalyst in a solution of dichloromethane (DCM) to provide a protected hydroxy-oxybenzone derivative.

13. The method of claim 12, wherein the protected hydroxy-oxybenzone derivative provided by the Friedel-Crafts acylation reaction is reacted with a silyl-protected version of a chloroethylene ether chain to provide a deprotected ethyl ether linked protected-oxybenzone.

14. The method of claim 13, wherein the silyl protecting group is removed by acidic conditions to provide an exposed terminal hydroxyl group that is converted to a phosphoric acid by reaction with a phosphorus and chlorine containing compound.

15. The method of claim 14, wherein the terminal hydroxyl group that was converted to said phosphoric acid directly binds to said oxide-containing particle.

16. The method of claim 10, wherein the benzophenone derivative with the oxide-containing particle having said microscale has a size ranging from 10 microns to 100 microns.

17. The method of claim 14, wherein following said removal of the silyl group, the benzophenone including composition has said terminal hydroxyl group converted to a bromide, wherein the bromide is directly bound to the metal oxide particle by nucleophilic substitutional chemistry.

* * * * *